(12) United States Patent
Fisher et al.

(10) Patent No.: US 8,844,528 B2
(45) Date of Patent: Sep. 30, 2014

(54) BREATHING CIRCUITS TO FACILITATE THE MEASUREMENT OF CARDIAC OUTPUT DURING CONTROLLED AND SPONTANEOUS VENTILATION

(76) Inventors: Joseph Fisher, Toronto (CA); David Preiss, Toronto (CA); Takafumi Azami, Toronto (CA); Alex Vesely, Toronto (CA); Eitan Prisman, Toronto (CA); Steve Iscoe, Toronto (CA); Ron Somogyi, Toronto (CA); Dan Nayot, Toronto (CA); Tehilla Adams, Toronto (CA)

( * ) Notice: Subject to any disclaimer, the term of this patent is extended or adjusted under 35 U.S.C. 154(b) by 2422 days.

(21) Appl. No.: 10/545,519

(22) PCT Filed: Feb. 18, 2004

(86) PCT No.: PCT/CA2004/000220
§ 371 (c)(1),
(2), (4) Date: Dec. 1, 2006

(87) PCT Pub. No.: WO2004/073779
PCT Pub. Date: Sep. 2, 2004

(65) Prior Publication Data
US 2007/0062534 A1    Mar. 22, 2007

(30) Foreign Application Priority Data
Feb. 18, 2003    (CA) .................................. 2419575

(51) Int. Cl.
*A62B 7/04*     (2006.01)
*F15C 1/08*     (2006.01)

(52) U.S. Cl.
USPC ................. 128/204.28; 128/204.24

(58) Field of Classification Search
USPC .......... 128/205.17, 205.15, 909, 910, 204.29, 128/204.18, 204.26, 204.28, 205.24, 128/203.25, 205.11, 914, 204.21–204.23, 128/205.12–205.13, 911
See application file for complete search history.

(56) References Cited

U.S. PATENT DOCUMENTS

| 3,901,230 | A | * | 8/1975 | Henkin | 128/205.17 |
| 4,098,271 | A | * | 7/1978 | Maddock | 128/202.22 |
| 4,883,051 | A | * | 11/1989 | Westenskow et al. | 128/204.21 |
| 5,197,481 | A | * | 3/1993 | Fisher | 600/532 |
| 5,694,924 | A | * | 12/1997 | Cewers | 128/204.21 |
| 6,340,024 | B1 | * | 1/2002 | Brookman et al. | 128/201.25 |
| 6,510,851 | B2 | * | 1/2003 | Rydin et al. | 128/204.21 |

(Continued)

FOREIGN PATENT DOCUMENTS

GB    2368531 A    5/2002
WO    WO 01/74433 A1    10/2001

(Continued)

OTHER PUBLICATIONS

Sasano et al., "A Simple Apparatus for Accelerating Recovery from Inhaled Volatile Anesthetics", Anesth Analg, 2001, pp. 1188-1191 No. 93, Int'l Anesthesia Research Society.

*Primary Examiner* — Rachael Young
(74) *Attorney, Agent, or Firm* — Herman & Millman

(57) ABSTRACT

A breathing circuit for sequential gas delivery of a first gas set (FGS) and a second gas set (SGS) employs an arrangement of conduits and active or passive valves to prevent mixing of the FGS and SGS including a valve triggered by depletion of FGS that makes the SGS available for inspiration after the FGS is depleted.

19 Claims, 17 Drawing Sheets

(56) References Cited

U.S. PATENT DOCUMENTS

| | | | |
|---|---|---|---|
| 6,612,308 B2 * | 9/2003 | Fisher et al. | 128/205.11 |
| 6,622,725 B1 | 9/2003 | Fisher et al. | |
| 6,662,802 B2 * | 12/2003 | Smith et al. | 128/203.16 |
| 2002/0185129 A1 * | 12/2002 | Fisher et al. | 128/203.25 |
| 2003/0075176 A1 * | 4/2003 | Fukunaga et al. | 128/203.12 |

FOREIGN PATENT DOCUMENTS

| | | |
|---|---|---|
| WO | WO 02/072185 A1 | 9/2002 |
| WO | WO 02/089888 A2 | 11/2002 |
| WO | WO 03/082390 A1 | 10/2003 |

* cited by examiner

Schematic diagram of circle anaesthetic circuit
Prior Art

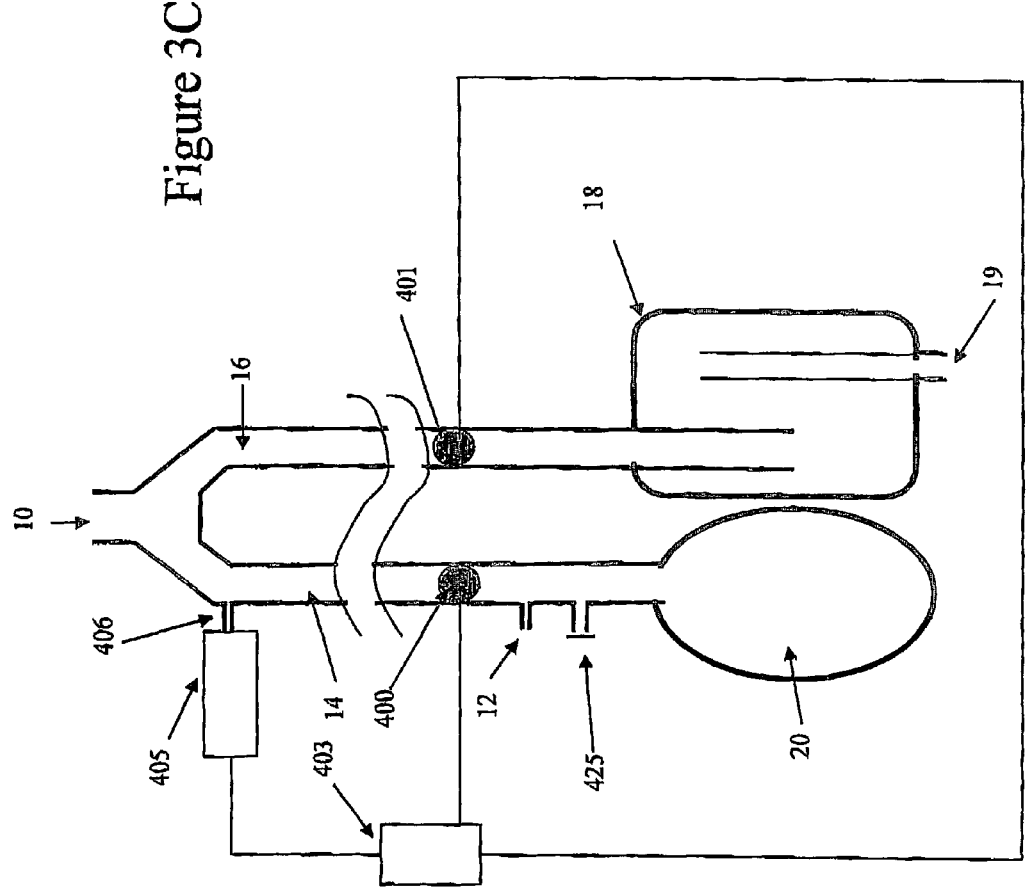

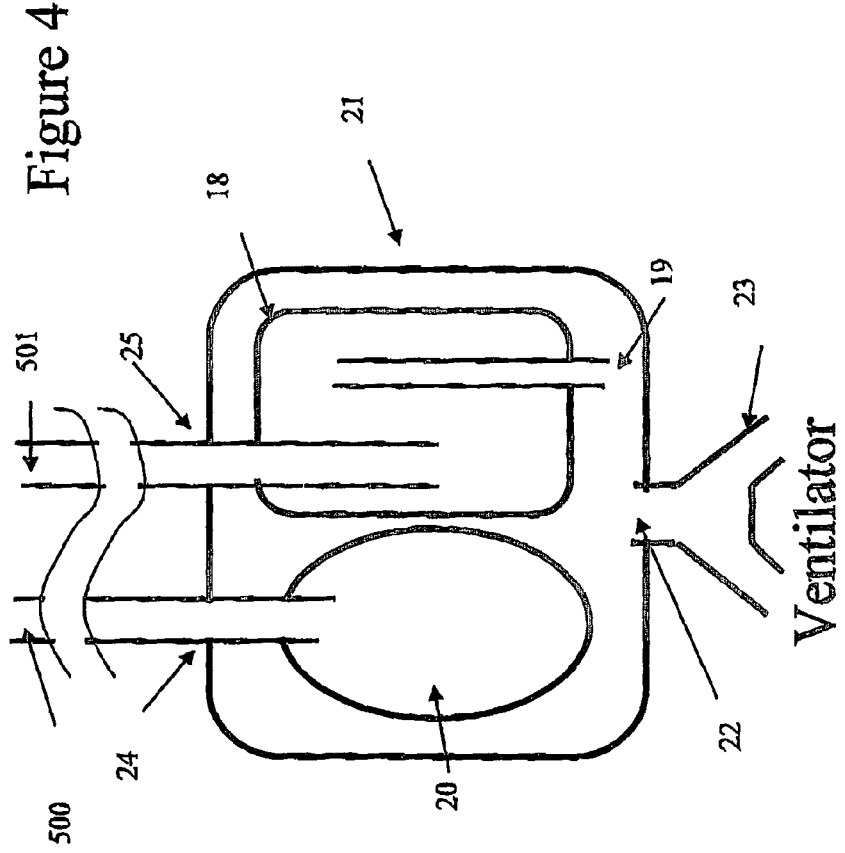

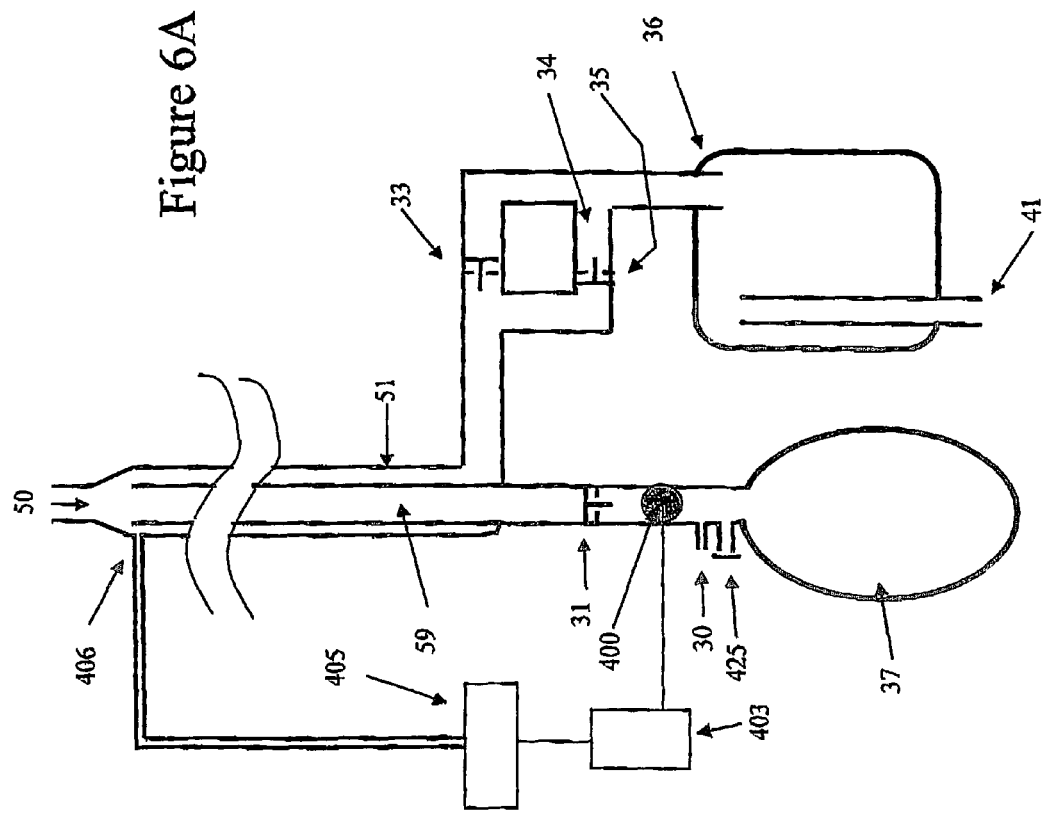

BREATHING CIRCUITS TO FACILITATE THE MEASUREMENT OF CARDIAC OUTPUT DURING CONTROLLED AND SPONTANEOUS VENTILATION

This application is a Continuation-In-Part Application of U.S. application Ser. No. 10/509,068 filed Mar. 17, 2005 the contents of which the application is incorporated herein by reference.

BACKGROUND OF THE INVENTION AND PRIOR ART

It is desirous to have an apparatus capable of measuring cardiac output in a non-invasive way. Several breathing circuits have been employed in the non-invasive measurement of cardiac output ($\dot{Q}$). For example, Gedeon in 1980 described a method of calculating $\dot{Q}$ in ventilated patients using the equation $$\dot{Q} = \frac{\dot{V}CO_2 - \dot{V}CO_{2'}}{P_{ET}CO_{2'} - P_{ET}CO_2}$$

where $P_{ET}CO_2$ and $P_{ET}CO_2'$ are the end tidal $PCO_2$ resulting from a change in $CO_2$ elimination from the lung ($\dot{V}CO_2$) from $\dot{V}CO_2$ to $\dot{V}CO_2'$ respectively. To perform the method, a breathing circuit is required that can impose a step change in $CO_2$ elimination in the lungs. The change in $\dot{V}CO_2$ is sustained for about one blood recirculation time, or about 30 s. Orr et al. reduced lung $CO_2$ elimination by using a breathing circuit where a dead space is temporarily interposed between the ventilator and the patient's airway resulting in a transient period of rebreathing previously exhaled gas. This is presently the method used by a commercially available product produced by Respironics. Rebreathing previously exhaled gas does not eliminate $CO_2$ from the lung so the $CO_2$ elimination is reduced proportional to the part of the minute ventilation that is constituted by rebreathed gas. The main limitation of the breathing circuits and methods proposed by Gedeon and Orr is that they can only be used in mechanically ventilated patients, as ventilated patients will increase their breath size or breathing frequency to compensate for the reduction in ventilation induced by inhaling the rebreathed gas.

OBJECT OF THE INVENTION

It is a primary object of this invention to provide circuits which will allow for easier and more precise control of the volume of absorption or elimination of $CO_2$ or any other gas such as $O_2$ or anesthetic vapor, from or to the lung respectively in both spontaneously breathing and mechanically ventilated patients.

A further object of this invention to describe breathing circuits which will allow for easier and more precise measurement of cardiac output in both spontaneously breathing and mechanically ventilated patients.

It is yet a further object of this invention to provide circuits which will allow for measurement and control of such physiologic parameters where the circuit allows more extensive access to the patient during surgical or other procedures, and with a more comfortable patient interface.

It is yet a further object of this invention to provide circuits which will allow for improved measurement and control of such physiologic parameters as alveolar ventilation of $CO_2$, $O_2$, and other gases entering the circuits.

It is yet a further object of this invention to provide circuits which completely separate a first gas set (FGS) entering the circuit and a second gas set (SGS), where FGS consists of a gas or mixture of gases and SGS consists of a gas or mixture of gases which may include previously exhaled gases or components of previously exhaled gases.

It is yet a further object of this invention to provide circuits which will allow for improved measurement and control of such physiologic parameters as alveolar ventilation of $CO_2$, $O_2$, and other gases entering the circuits while using modified previously exhaled gas as SGS.

It is yet a further object of this invention to provide circuits which will allow for improved measurement and control of such physiologic parameters as alveolar ventilation of $CO_2$, $O_2$, and other gases entering the circuits during anesthesia.

Further and other objects of the invention will become apparent to those skilled in the art when considering the following summary of the invention and the more detailed description of the preferred embodiments illustrated herein.

SUMMARY OF THE INVENTION

Fisher described another partial rebreathing circuit in U.S. Pat. No. 6,622,725 for maintaining end-tidal $PCO_2$ constant despite increasing minute ventilation. A schematic of the Fisher circuit is shown in FIG. 2. When breathing via the Fisher circuit, and minute ventilation ($\dot{V}E$) exceeds the flow of a fresh gas (containing no $CO_2$) into the circuit. Exhaled gas is stored in an exhaled gas reservoir (18) and is available for rebreathing. The volumes of rebreathed gas inhaled is proportional to the portion of $\dot{V}E$ that exceeds the fresh gas flow resulting in no increase in the elimination of $CO_2$ as a result of increases in $\dot{V}E$. Under these circumstances, the alveolar ventilation and the wash-out of $CO_2$ from the lung is predominantly a function of the fresh gas flow into the circuit, and not the $\dot{V}E$. Therefore, by inducing a step reduction in fresh gas flow, one can induce a step reduction in alveolar ventilation for $CO_2$ and thereby a transient reduction in $\dot{V}CO_2$. To generate the data required to calculate $\dot{Q}$ by the differential Fick method described by Gedeon, this reduction in fresh gas flow is maintained for approximately one recirculation time (~30 s) and returned to a value equal to or greater than $\dot{V}E$. $\dot{Q}$ is then calculated as follows: the $\dot{V}CO_2$ and fractional concentration of exhaled $CO_2$ ($F_{ET}CO_2$) are measured prior to the reduction in the fresh gas flow. The reduced fresh gas flow (which is equal to the alveolar ventilation) times $F_{ET}CO_2$ will equal the $\dot{V}CO_2'$ and the $P_{ET}CO_2$ at the end of the period of reduced fresh gas flow provides the value for $P_{ET}CO_2'$ to complete the requirements for the differential Fick equation.

A brief description of the partial rebreathing circuit described by Fisher (FIG. 2) follows: During exhalation, gas passes from the patient port (10), through the expiratory one-way check valve (15) down the expiratory limb (16) into the expiratory reservoir bag (18). Excess gas exits the expiratory reservoir bag (18) at the opening (19). Fresh gas (in this case gas containing no $CO_2$) enters the circuit at a constant flow via a fresh gas port (12). As the inspiratory one-way check valve (11) is closed during exhalation, the fresh gas accumulates in the fresh gas reservoir bag (20). During inhalation, fresh gas entering from the port (12) and the fresh gas reservoir (20) passes through the inspiratory valve (11) and enters the patient. If the fresh gas flow is less than $\dot{V}E$, the fresh gas reservoir bag (20) collapses and valve (17) in the bypass limb (13) opens, directing previously exhaled gas to the patient.

Important characteristics of the circuit
1) there are 3 valves, inspiratory, expiratory, and a bypass valve which bypasses the expiratory valve.
2) during exhalation, it mostly prevents mixing of exhaled gas with fresh gas
3) when minute ventilation ($\dot{V}_E$) exceeds fresh gas flow, both fresh gas and previously expired gas are inhaled in sequence-fresh gas first followed by mostly previously expired gas.

Although the Fisher circuit can be used to measure cardiac output as described above, the circuit has a number of drawbacks and features suboptimal for inducing known changes in $\dot{V}CO_2$. We describe an additional series of new circuits which address these drawbacks and deficiencies.

We define a class of circuits, to which the Fisher circuit belongs, as sequential gas delivery breathing (SGDB) circuits. We denote the gas delivered first to the patient in a SGDB circuit as the First Gas Set (FGS) which consists of a set of component gases such as $O_2$, N2, $CO_2$, and other gases and vapors according to the desired alveolar gas concentrations of these component gases, the second gas set (SGS), which consists of a set of component gases such as $O_2$, N2, $CO_2$, and other gases and vapors which is delivered during inhalation sequentially after FGS when the patient's ventilation exceeds the flow of FGS and the patient continues to inhale. Each gas set can be composed of one or more gases or vapors. The SGS can be previously exhaled gas previously exhaled gas modified by removing component gas or gases, or adding component gas or gases prior to inhaling SGS. All SGDB circuits have the additional following characteristics in common
  a) the flow of FGS into the circuit (FGSP) is one determinant of alveolar ventilation for a component gas, and with respect to $CO_2$, it is a determinant of $CO_2$ elimination;
  b) the partial pressure of component gases in FGS and SGS, for example, $CO_2$ ($PCO_2$), can be set to any value. If the $PCO_2$ in FGS is practically 0, as it would be in room air or $O_2$ from a compressed gas $O_2$ cylinder, all of FGSF would contribute directly to $CO_2$ elimination. When SGS consists of previously exhaled gas, the partial pressure of component gases are such that they contribute minimally to flux of those gases in the lung. For example, when the $PCO_2$ of SGS is equal to alveolar $PCO_2$, inhaled SGS does not contribute to $CO_2$ elimination during breathing. Thus, in SGDB circuits where FGSF is restricted, and the balance of inhaled gas consists of previously exhaled gas, SGS gas does not contribute to gas flux and there is a direct relationship between the FGS flow and composition on the one hand, and gas flux on the other. With respect to $CO_2$, when SGS consists of previously exhaled gas, $PCO_2$ of SGS is assumed to be equal to that in the alveoli and $CO_2$ elimination from the lung is a function of FGSF only (assuming $PCO_2$ of FGS is fixed). Therefore a step change in FGS flow into a SGDB circuit results in a step change in $CO_2$ elimination from the lung.

The circuit as taught by Fisher falls into the category of SGDB circuit. However, this circuit has features that limit its suitability for changing $\dot{V}_A$ and thereby generating the data for measuring cardiac output via the differential Fick method of Gedeon.
1) The manifold of 3 valves must be close to the patient's airway in order to minimize the effect of equipment deadspace and retain the characteristics of sequential delivery of gas on each breath. Positioning the manifold close to the patient airway is problematic when the patient's head is in a confined space (such as MRI cage, or during ophthalmologic examination) or when extensive access to the head and neck is required such as during surgery, or in many other cases where it is advantageous to measure cardiac output. Moving the manifold in this circuit remote from the patient presents the following problem. While the fresh gas reservoir bag (20) and expiratory gas reservoir bag (18) can be moved remotely, as shown in FIG. 3, the inspiratory valve (11), expiratory valve (15), or bypass valve (17) must be kept close to the patient port (10) in order to retain the advantages of the $FIC_1$ in maintaining isocapnia. Moving the valves and bypass limb distally from the patient will result in previously exhaled gas mixing with fresh gas in the inspiratory limb (14) before it is delivered to the patient. The precise sequential delivery of gases will be lost.
2) The valve in the bypass limb is designed to open during inspiration after the fresh gas reservoir collapses. The resistance in this valve has to be low in order to minimize the resistance to inspiration. With vigorous exhalation, as occurs during exercise or after a cough or sigh, the pressure in the expiratory limb may rise sufficiently to open the bypass valve and blow some expired gas into the inspiratory limb. The expired gas in the inspiratory limb displaces the same volume of fresh gas so on the next breath both fresh gas and previously exhaled gas enter the lungs together rather than in sequence.
3) When the fresh gas reservoir collapses and the patient is rebreathing previously exhaled gas, the fresh gas enters the fresh gas port and rather than refilling the bag, will mix with the rebreathed gas coming through the bypass valve. This alters the concentration of rebreathed gas so as to make it impossible to precisely measure and control physiologic $\dot{V}_A$ and $P_{ET}CO_2$.
4) It cannot be used to during anesthesia with anesthetic vapors
5) The configuration of the circuit does not lend itself to the addition of a gas absorber on the bypass limb, a change required in order to use a SGDB circuit to deliver anesthetics efficiently at low FGSFs and thus allow the determination of $\dot{Q}$ during anesthesia. Placing a $CO_2$ absorber on a bypass limb of a circuit would make the manifold even more bulky and further restrict access to the head.
6) It can be used only with spontaneous ventilation.
7) There is no means to effect heat and moisture exchange between inhaled and exhaled gases None of the other partial rebreathing circuits known in the art are suitable for instituting a stable step change in $\dot{V}CO_2$ in spontaneously breathing patients, where such patients can change their pattern of ventilation and thereby circumvent an attempt to induce a stable change in their $\dot{V}CO_2$.

We herein describe a set of new circuits that deliver FGS and SGS sequentially during inhalation whenever $\dot{V}_E$ exceeds the FGS flow into the circuit and have one or more further practical advantages over previously taught circuits with respect to use on subjects or patients to control the alveolar concentration of gases as a result of the following features:
  the valves and gas reservoir bags are remote from the interface with the patient without affecting the ability of the circuit to sequentially deliver FGS then SGS gas during inhalation whenever $\dot{V}_E$ exceeds the FGSF.
  the nature and/or configuration of the valves precludes any of the SGS entering the inspiratory limb of the circuit even after a vigorous exhalation.
  the circuits can be used with spontaneous ventilation or controlled ventilation.

The circuits can be configured such as inspiratory and expiratory limbs are arranged co-axially, providing the advantages of compactness, and heating/moisturizing of inspired gas They allow for the precise control of fluxes of any of the component gases of FGS and SGS according to the concentrations of the component gases of FGS and SGS and the flow of FGS.

they allow for improved control of $\dot{V}CO_2$ during the test and improved accuracy of measurement of end tidal gas concentrations and thereby improve the accuracy and precision of noninvasive measurements of cardiac output they can be used to measure cardiac output and delivering vapor anesthetic in spontaneously breathing or ventilated subjects

BRIEF DESCRIPTION OF THE FIGURES

FIG. 3C is similar to FIG. 3B wherein an active valve has replaced the passive inspiratory valve.

FIG. 4 shows a modification of any of the circuits shown in FIGS. 2, 3-3E, 5-5B for use with a mechanically ventilated patient.

DESCRIPTION OF THE INVENTION

Figure 5:
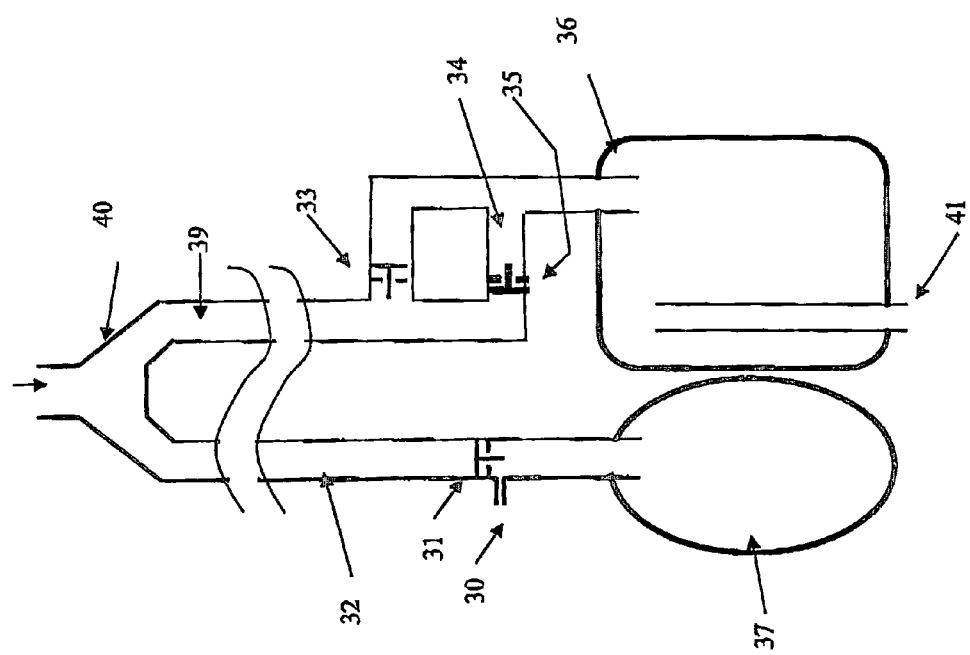
FIG. 5 is a new circuit for use with spontaneous ventilation

Description of Circuit with Valves and Reservoirs Distal From Patient, and Precludes the Contamination of FGS with SGS Through Bypass Valve FIG. 5 shows a breathing circuit which provides sequential delivery of the FGS followed by the SGS when $\dot{V}_E$ exceeds FGSF, with the manifold containing the valves and the FGS reservoir bag and the expiratory gas reservoir bag remote from the patient. This improvement reduces the bulk of the patient manifold, and eliminates the possibility of the SGS mixing with the FGS due to vigorous exhalation.

Referring to FIG. 5, Patient (38) breathes via a Y connector (40). Valve (31) is an inspiratory valve and valve (33) is an expiratory valve. Valve (35) is a bypass valve in the bypass limb (34) that bypasses the expiratory valve (33) and has an opening pressure greater than inspiratory valve (31). Valves (35, 33) may be close to or distal from the patient manifold as desired, as long as they are on the expiratory limb (39). However, in the preferred embodiment, they are distal to the patient to reduce the bulk of the patient manifold. Inspiratory valve (31) may be close to, or distal from, the patient manifold as desired, as long as it is on the inspiratory limb (32). In the preferred embodiment, it is distal to the patient as well. FGS enters the circuit via port (30).

Function:

During exhalation, increased pressure in the circuit closes inspiratory valve (31) and bypass valve (35). Gas is directed into the exhalation limb (39), past one-way valve (33) into the expiratory gas reservoir bag (36). Excess gas is vented via port (41) in expiratory gas reservoir bag (36). FGS enters via port (30) and fills FGS reservoir (37). During inhalation, inhalation valve (31) opens and FGS from the FGS reservoir (37) and FGS port (30) enter the inspiratory limb (32) and are delivered to the patient. If FGSF is less than $\dot{V}_E$, the FGS reservoir (37) empties before the end of the breath, and continued respiratory effort results in a further reduction in pressure in the circuit. When the opening pressure of the bypass valve (35) is reached, it opens and gas from the expiratory gas reservoir (36) passes into the expiratory limb (39) and makes up the balance of the breath with SGS.

Thus when FGSP is less than $\dot{V}_E$, the subject inhales FGS, then SGS, and no contamination of FGS occurs.

Figure 3:
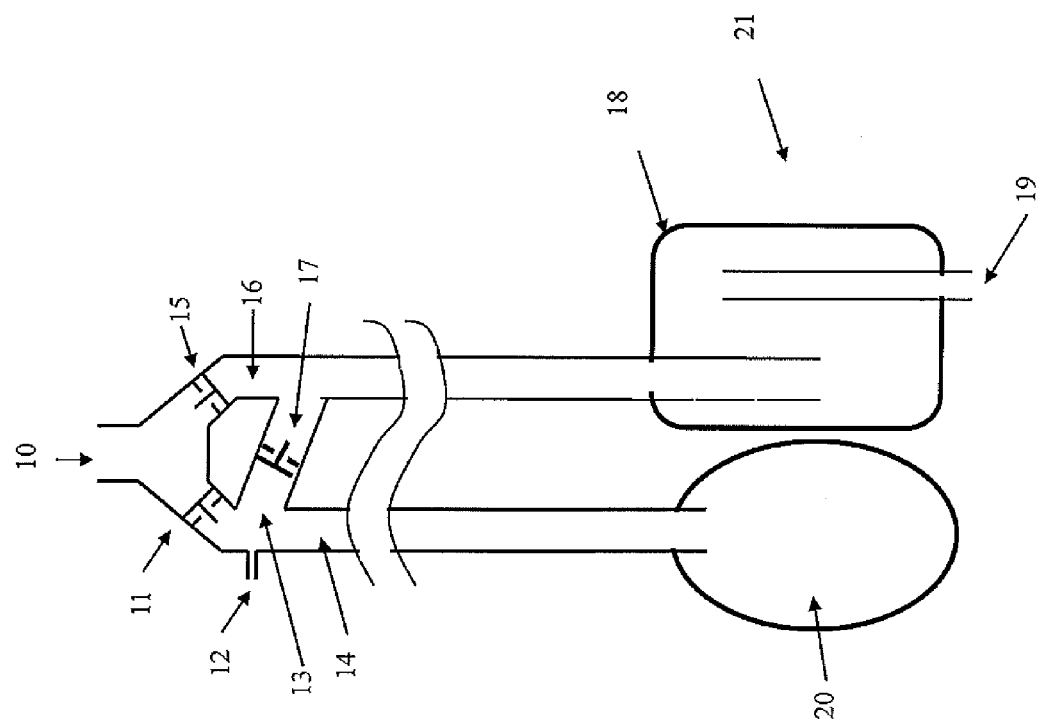
FIG. 3 is similar to FIG. 2 wherein the reservoir bags are remote from the patient.
Figure 3B:
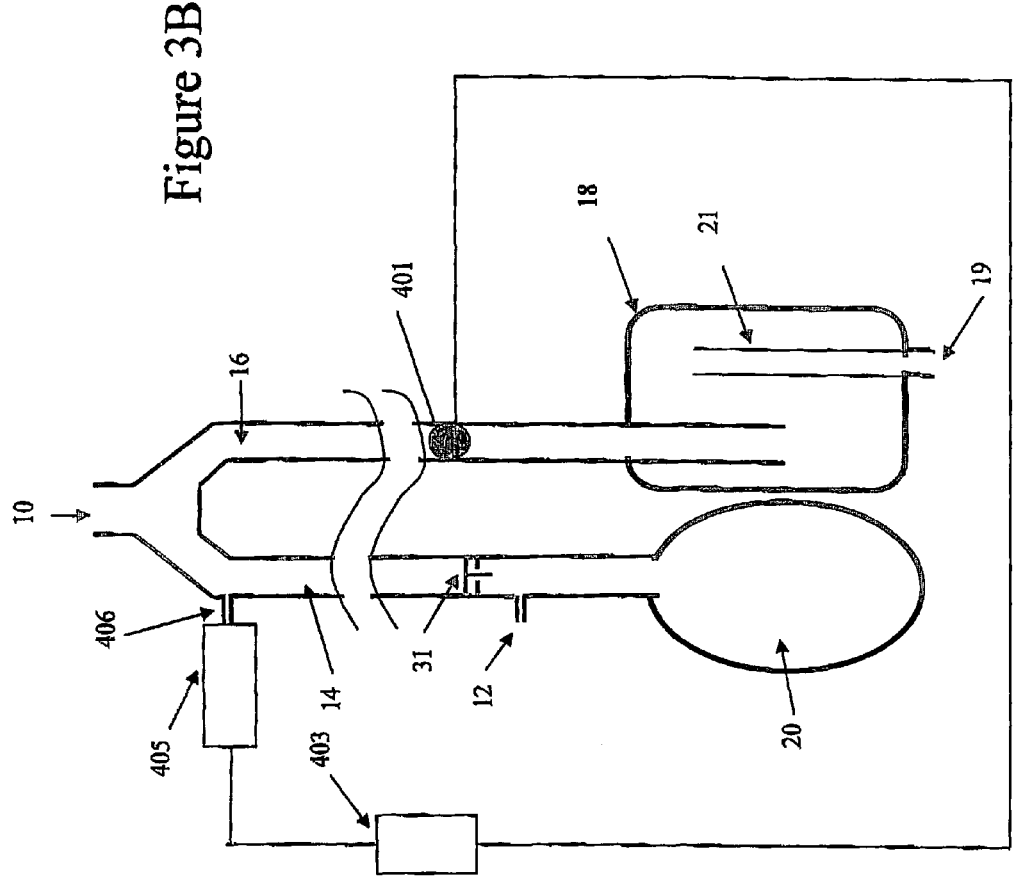
FIG. 3B is similar to FIG. 5 wherein bypass limb, bypass valve, and passive expiratory valve are replaced by an active expiratory valve.

FIG. 3B shows an alternate embodiment of the circuit illustrated in FIG. 5 where the passive expiratory valve (33) and expiratory bypass limb (34), and expiratory limb bypass valve (35) are replaced with a control valve that is triggered by the collapse of the inspiratory reservoir. Referring to FIG. 3B, a control valve (401) is placed in the expiratory limb (16) anywhere along its length between the patient port (10) and the expiratory reservoir bag (18). When the patient's $\dot{V}_E$ exceeds the FGSF during inspiration the reservoir bag (20) collapses. This is detected by pressure sensing means (405) through port (406) as an acute reduction in pressure. Pressure sensing means (405) could be an electronic pressure transducer capable of detecting changes 2 cm $H_2O$ pressure, for example. Immediately afterwards, valve (401) is then opened by control means (403), which could be an electronic signal for activating a solenoid valve, for example, leading to depressurization and collapse of a balloon valve, as is known to those skilled in the art, resulting in SGS is being inhaled for the balance of inhalation. During exhalation, patient exhales through expiratory tube (16) past valve (401) into the SGS reservoir (18). At end of exhalation, as detected by pressure sensing means (405) as a reduction of pressure, valve (401) is closed by control means (403), which could be an electronic signal for toggling a solenoid valve, for example, leading to pressurization and inflation of a balloon valve, as is known to those skilled in the art.

Use of Control Valve in Inspiratory Limb to Prevent FGS Contaminating SGS

While the circuits of FIG. 5 and FIG. 3B present the advantages over the Fisher circuit of reducing the bulk of the patient manifold, and eliminating the possibility of the SGS mixing with the FGS due to vigorous exhalation, they still have the following drawback: When FGS reservoir (20, 37) is emptied and the patient is breathing SGS for the balance of an inspiration, the circuit does not deliver SGS alone but a mixture of SGS and FGS. The FGS continues to flow into the circuit and is drawn by inhalation past one-way inspiratory valve (31,3) and allows FGS gas to be inhaled from the inspiratory limb (32,14). To optimize the generation of data required to measure of cardiac output, it is necessary to redirect the FGS into the FGS reservoir ((37,20) for the balance of inhalation after the initial collapse of the FGS reservoir. This would prevent mixing of FGS with SGS during the period of inhalation where the patient breathes SGS. This limitation of circuits illustrated in FIGS. 5 and 3B with respect to measuring cardiac output are shared with the Fisher circuit.

Figure 3D:
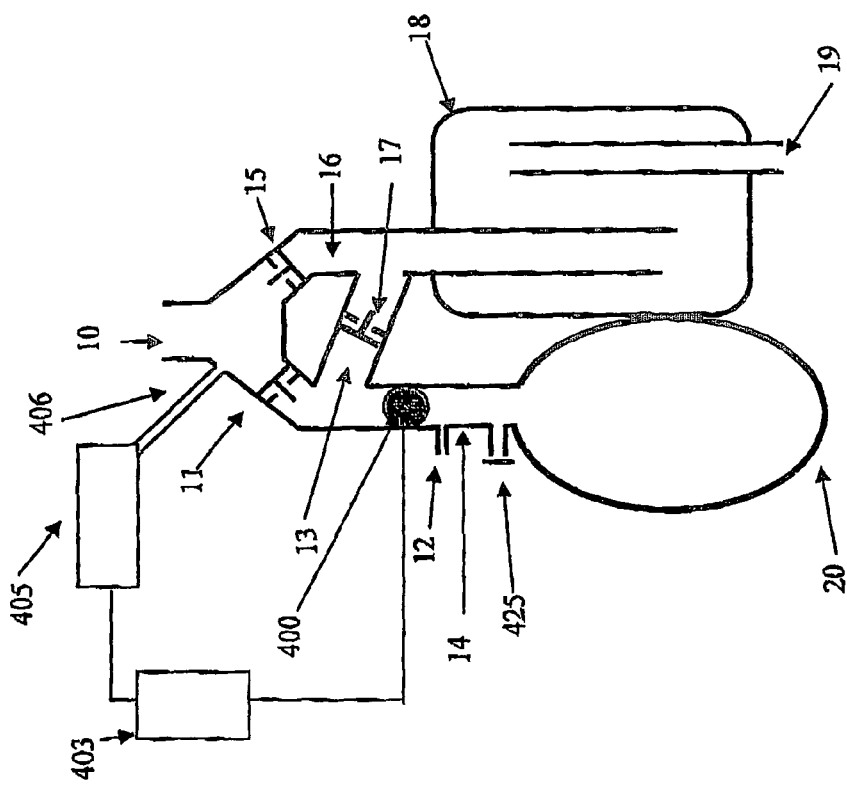
FIG. 3D is similar to FIG. 2 wherein an active valve has been added to the inspiratory limb to prevent mixing of FGS with SGS during inhalation.

FIG. 3D shows an improved circuit that prevents contamination of the SGS by FGS when SGS is being delivered to the patient. Referring to FIG. 3D, FGS control valve (400) is added to the inspiratory limb (14) at some point between the FGS port (12) and the inspiratory valve (11). Pop-off valve (425) is connected to the inspiratory limb on the side of the FGS control valve (400) that is proximal to the inspiratory reservoir bag (425). During exhalation, gas passes from the patient port (10), through the expiratory one-way check valve (15) down the expiratory limb (16) into the expiratory reservoir bag (18). Excess gas exits the expiratory reservoir bag (18) at the opening (19) remote from the entrance. FGS enters the circuit at a constant flow via a fresh gas port (12). As the inspiratory one-way check valve (11) is closed during exhalation, the fresh gas accumulates in the fresh gas reservoir bag (20). During inhalation, FGS entering from the port (12) and the FGS reservoir (20) passes through the inspiratory valve (11) and enters the patient. If the FGSF is less than $\dot{V}_E$, the FGS reservoir bag (20) collapses, as detected by pressure sensing means (405) connected to pressure sensing port (406). FGS control valve (400) is closed via valve control means (403), and valve (17) in the bypass limb (13) opens, directing previously exhaled gas to the patient. When the FGS control valve (400) is closed, any FGSF entering the circuit during the balance of inspiration is directed only to the FGS reservoir bag (20) and not to the patient, who is receiving SGS for the balance of inspiration. FGS control valve (400) may be re-opened any time from the beginning of expiration to just before the next inspiration. FGS control valve (400) may be any type of valve, and is preferably an active valve such as a balloon valve, known to those skilled in the art, that can be controlled by automated means. The pop-off valve (425) opens when the reservoir bag (20) is full to prevent the reservoir bag (20) from overfilling.

Figure 5A:
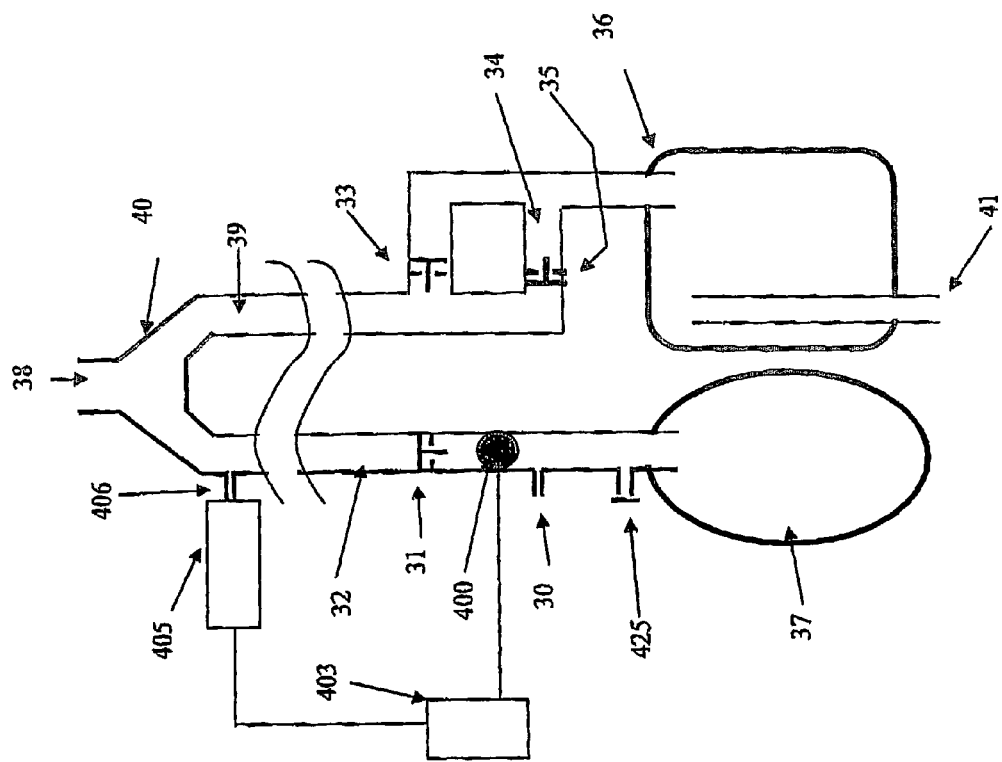
FIG. 5A is similar to FIG. 5 wherein an active valve has been added to the inspiratory limb to prevent mixing of FGS with SGS during inhalation.

The circuit illustrated in FIG. 5A is similar to that in FIG. 5 but has the addition of a FGS control valve (400), together with pressure sensing means (405) and port (406), and valve control means (403), added to the inspiratory limb of the circuit (32) distal to the one-way inspiratory valve (31) and proximal to the FGS inflow port (30). Similarly, a FGS control valve, together with pressure sensing means and port, and valve control means, may be added to the inspiratory limb (14) of the circuit illustrated in FIG. 3B positioned distal to the one-way inspiratory valve (31) and proximal to the FGS inflow port (12) to achieve the same result, namely, prevention of contamination of SGS by FGS when $\dot{V}_E$ exceeds FGSF and the FGSF reservoir bag is emptied.

FGS Control Valve Replacing Inspiratory Valve

Figure 3E:
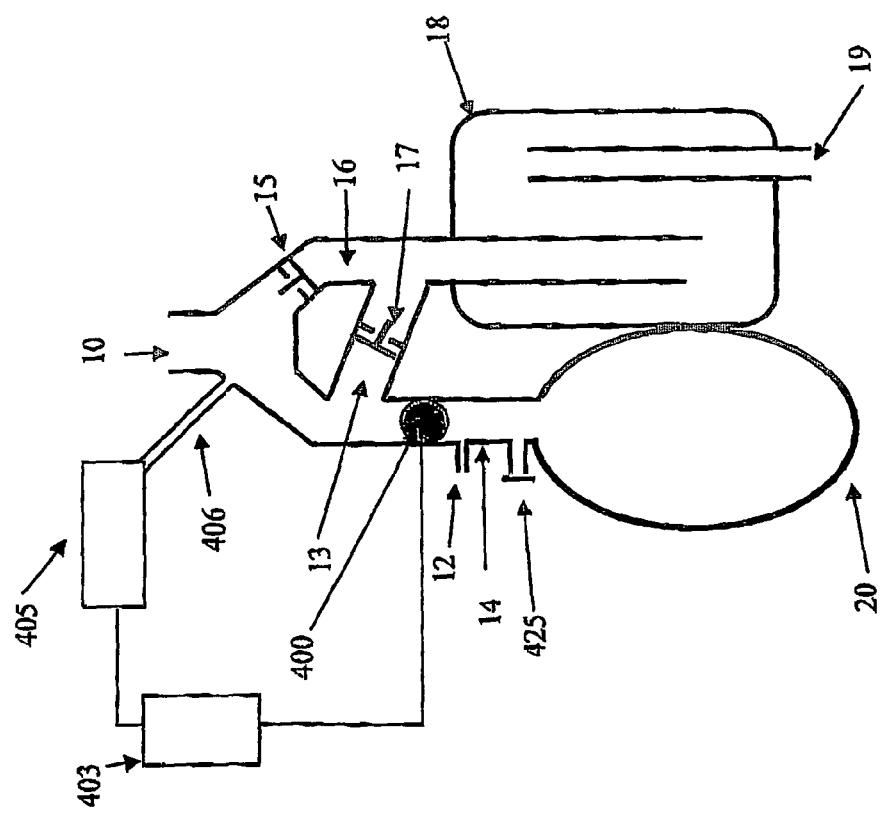
FIG. 3E is similar to FIG. 2 wherein an active valve has replaced the passive inspiratory valve.
Figure 5B:
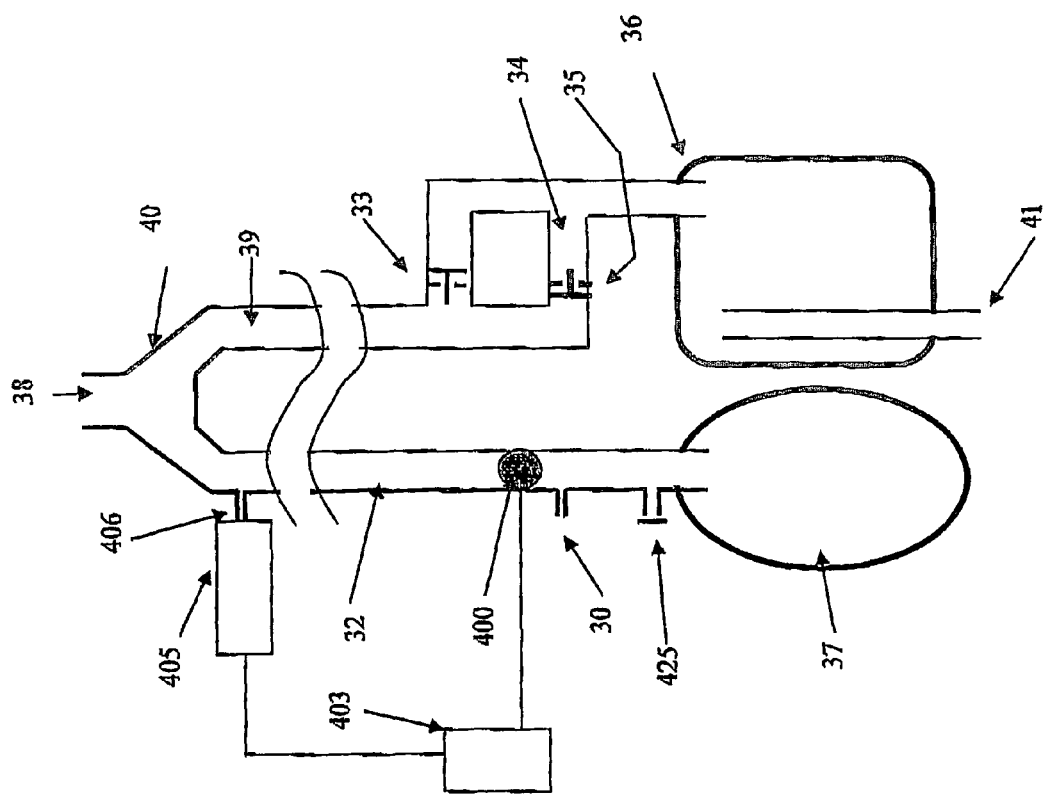
FIG. 5B is similar to FIG. 5 wherein an active valve has replaced the passive inspiratory valve.
Figure 5C:
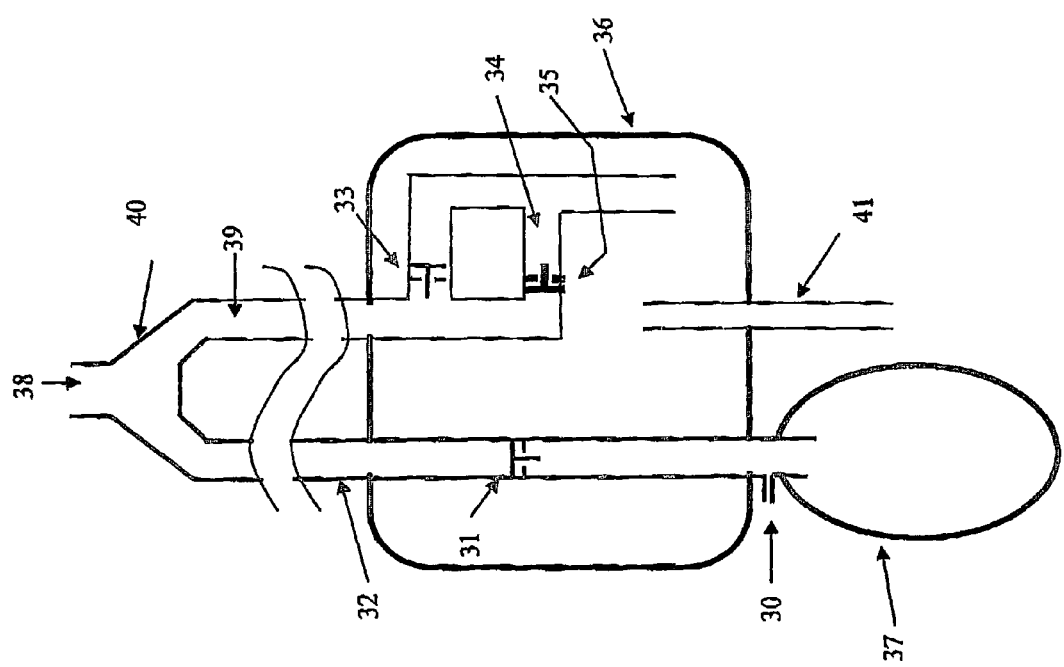
FIG. 5C shows a detail of a circuit design where the passive valves are surrounded by the exhaled gas reservoir

We present two additional circuits that are configured by adding FGS control valve (400) together with pressure sensing means (405) and port (406), and valve control means (403), to the Fisher circuit and the circuit illustrated in FIG. 5 and removing the passive one way inspiratory valve (11, 31), as shown in FIGS. 3E and 5B respectively. These circuits function identically to those illustrated in FIGS. 3D and 5A with respect to complete separation of FGS and SGS during inhalation. In such a circuit, during inspiration, FGS control valve (400) is open until FGSF reservoir bag (20,37) is emptied, then it is dosed so that any additional FGSF entering the circuit during the balance of inspiration is directed only to the reservoir bag (20) and not to the patient. As the patient continues to inspire, bypass valve (17,35) opens allowing the patient to inhale SGS for the balance of inspiration.

Use of Co-Axially Arranged Inspiratory and Expiratory Limbs

Figure 6:
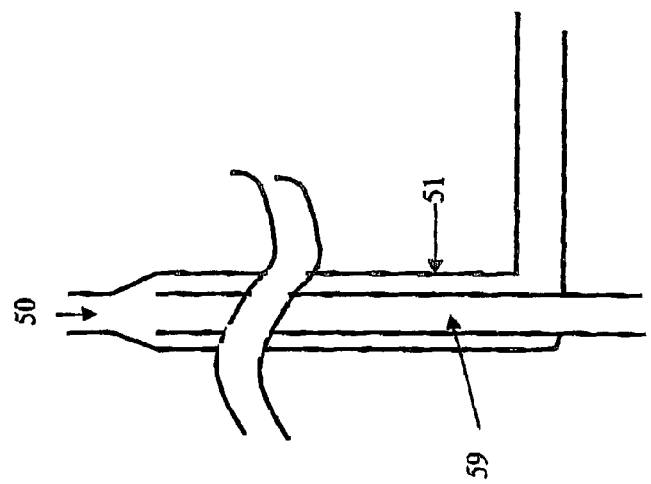
FIG. 6 is a modification of the above circuits to include co-axially arranged inspiratory and expiratory limbs between the valves and the patient FIG. 6A show the preferred embodiment of the cardiac output circuit where inspiratory and expiratory limbs are co-axially arranged with the circuit of FIG. 5A.

Another embodiment of each of the circuits whereby the valves can be remote from the patient without loss of sequential delivery of FGS and SGS, such as those illustrated in FIGS. 5,33B, 5A, 5B, 3C, 4B, is the replacement of separate inspiratory limbs and expiratory limbs with co-axially arranged inspiratory and expiratory limbs as shown in FIG. 6. FIG. 6A shows the preferred embodiment of the invention: The circuit valves are configured as in the circuit illustrated in FIG. 5A with the improvement of co-axially arranged inspiratory (59) and expiratory (51) limbs. The limbs (51, 59) are co-axial so that one limb is contained within the other for some length of tubing, with the limbs separating at some point along its length, such that the expiratory limb (51) leads to the exhaled gas reservoir (54) and the inspiratory limb (59) leads to the FGS reservoir (56). This has two important advantages over the circuit of FIG. 5:

1. A single tube is connected to the patient interface making it easier to manage sick patients
2. The heat contained in the expiratory limb (51) warms the FGS entering through the inspiratory limb (59).
3. If the inner tube is of a material that allows moisture to pass through it but not gas, such as Nafion, will promote moisture exchange as well, so that FGS will become slightly moisturized and more comfortable for the patient to breathe if the SGS is moist It should be understood that co-axial tubing may be used with any of the SGDB circuits described herein.

DESCRIPTION OF PREFERRED EMBODIMENT

Referring to FIG. 6A, Patient port (50) opens directly to the inspiratory limb (59) and expiratory limb (51) without a Y connector, where the limbs are arranged co-axially. Valve (31) is an inspiratory valve and valve (33) is an expiratory valve. Valve (35) is a bypass valve in the bypass limb (34) that bypasses the expiratory valve (33) and has an opening pressure greater than inspiratory valve (31). Valves (35, 33) are preferably distal from the patient on the expiratory limb (51) to reduce the bulk of the patient interface. Inspiratory valve (31) is also preferably distal from, the patient on the inspiratory limb (59). FGS enters the circuit via port (30). FGS control valve (400) is on the inspiratory limb (59) between port (30) and inspiratory valve (31). FGS reservoir bag (37) is connected to inspiratory limb (59) distal to the patient, past port (37). SGS reservoir bag (36) is distal to the patient on the expiratory limb (51) past expiratory valve (33) and bypass valve (35). Excess expiratory gas vents to the atmosphere via port (41). Pressure sensing means (405) is connected to pressure sensing port (406) which is connected to the patient port (50), and valve control means (403). Pressure sensing port (406) may be connected to the co-axial inspiratory (59) and expiratory limb arrangement (51) anywhere along its length between the inspiratory valve (31) and the patient port (50) or between the expiratory valve (33) and the patient. Pop-off valve (425) is connected to the inspiratory limb on the side of the FGS control valve (400) that is proximal to the inspiratory reservoir bag (425).

Function:

During exhalation, increased pressure in the circuit closes inspiratory valve (31) and bypass valve (35). Gas is directed into the exhalation limb (51), past one-way valve (33) into the expiratory gas reservoir bag (36). Excess gas is vented via port (41) in expiratory gas reservoir bag (36). FGS enters via port (30) and fills FGS reservoir (37). During inhalation, inhalation valve (31) opens and FGS from the FGS reservoir (37) and FGS port (30) enter the inspiratory limb (59) and are delivered to the patient. If FGSF is less than $\dot{V}_E$, the FGS reservoir (37) empties before the end of the breath, and continued respiratory effort results in a further reduction in pressure in the circuit. When the opening pressure of the bypass valve (35) is reached, it opens and gas from the expiratory gas reservoir (36) passes into the expiratory limb (39) and makes up the balance of the breath with SGS. The emptying of FGS reservoir bag (37) is detected by pressure sensing means (405) such as an electronic pressure transducer, known to those skilled in the art, connected to pressure sensing port (406), and FGS control valve (400) such as a balloon valve known to those skilled in the art, is closed via valve control means (403) such as access to gas pressure controlled by an electronically toggled solenoid valve known to those skilled in the art. When the FGS control valve (400) is closed, any additional FGSF entering the circuit during the balance of inspiration is directed only to the FGS reservoir bag (20) and not to the patient, who is inhaling only SGS for the balance of inspiration. FGS control valve (400) may be re-opened any time from the beginning of expiration, as sensed by the reverse of pressure by the pressure sensing means (405), to just before the next inspiration, also sensed by pressure changes in the breathing circuit. Pop-off valve (425) prevents the FGS reservoir bag (20) from overfilling when FGS exceeds $\dot{V}_E$.

Thus when FGSF is less than $\dot{V}_E$, the subject inhales FGS, then SGS, and no contamination of SGS with FGS occurs.

Use of Circuits for Ventilated Patients

Any of the SGDB circuits disclosed herein as well as the Fisher circuit can be used for a patient under controlled ventilation by enclosing the FGS reservoir (20) and exhaled gas reservoir (18) within a rigid container (21) with exit ports for the inspiratory limb of the circuit (24) and expiratory limb of the circuit (25) and port for attachment to a patient interface of a ventilator (22) as illustrated in FIG. 4. In FIG. 4, the inspiratory limb (500) represents the inspiratory limb of any of the SGDB circuits herein described, and expiratory limb (501) corresponds to the expiratory limb of any of the SGDB circuits herein described. The FGS reservoir bag (20) and expiratory gas reservoir bag (18) are enclosed in a rigid air-tight container such that the inspiratory limb (500) enters the container via port (24) and expiratory limb (501) enters the container via port (25) such that the junctions of the outside of the limbs form an air-tight seal with the inside surface of the ports. A further port (22) is provided for attachment of the Y piece of any ventilator (23). Detachment from the ventilator allows the circuit to be used with a spontaneously breathing patient. During the inspiratory phase of the ventilator, the pressure inside the container (21) rises putting the contents of the FGS reservoir bag (20) and the expiratory gas reservoir bag (18) under the same pressure. Since the opening pressure of the inspiratory valve is less than that of the bypass valve for circuits using passive bypass valves (for example those shown in FIGS. 2, 3, 5, 5B, 5A, 3E, and 3D), the FGS reservoir (20) will be emptied preferentially. When the FGS reservoir (20) is empty, the pressure in the container (21) and inside the expiratory gas reservoir (18) will open the bypass valve (35, 17, 206) and begin emptying exhaled gas reservoir (18) delivering SGS to the patient. For circuits using an actively engaged control valve (400) in the inspiratory limb of the circuit, a valve opening detection means (407) such as an electronic circuit that is broken by the opening of the valve when the valve is part of a closed electronic circuit, not shown, detects opening of the one way valve (35, 17, 206) in the exhalation bypass limb. The FGS control valve (400) is then closed, directing FGS into the FGS reservoir bag until the collapse of the FGS reservoir during the next inspiratory phase.

During the exhalation phase of the ventilator, the ventilator's expiratory valve is opened and contents of the container (21) are opened to atmospheric pressure, allowing the patient to exhale into the expiratory gas reservoir (18) and the FGS to flow into the FGS reservoir bag (20). Thus, the FGS and SGS are inhaled sequentially during inhalation with controlled ventilation without mixing of FGS with SGS at any time.

Figure 4B:
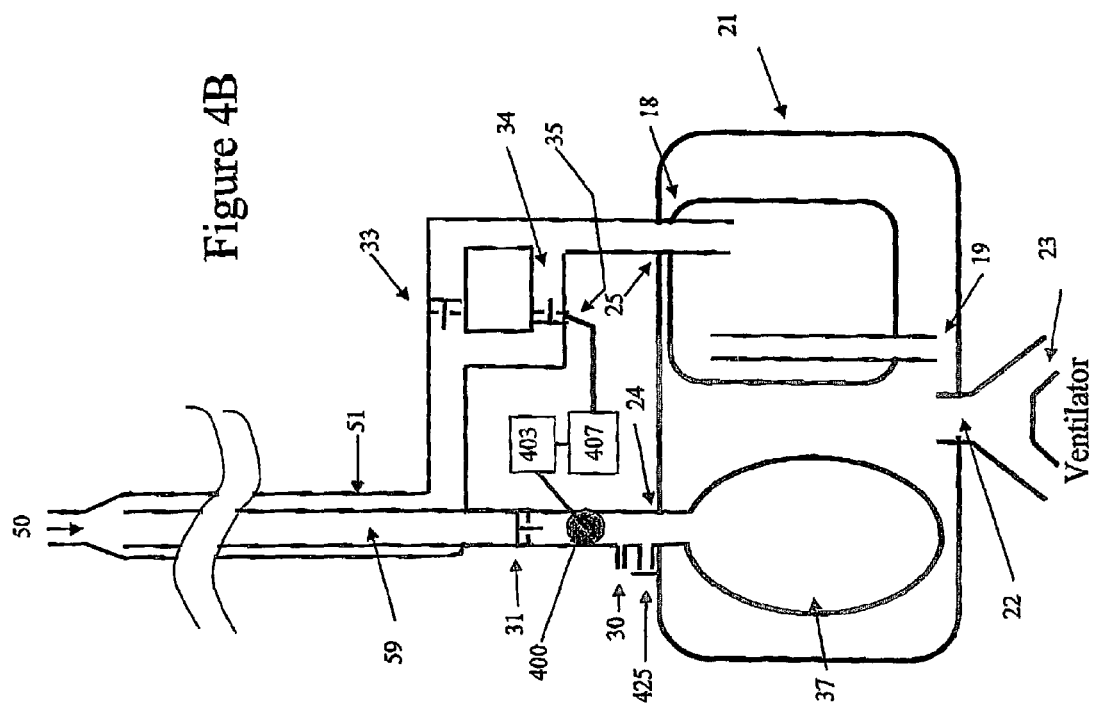
FIG. 4B shows the preferred embodiment modified for use on ventilated patients.

FIG. 4B shows the ventilator configuration described above as used with the preferred circuit shown in FIG. 6A. This is the preferred embodiment for ventilated patients.

Figure 1:
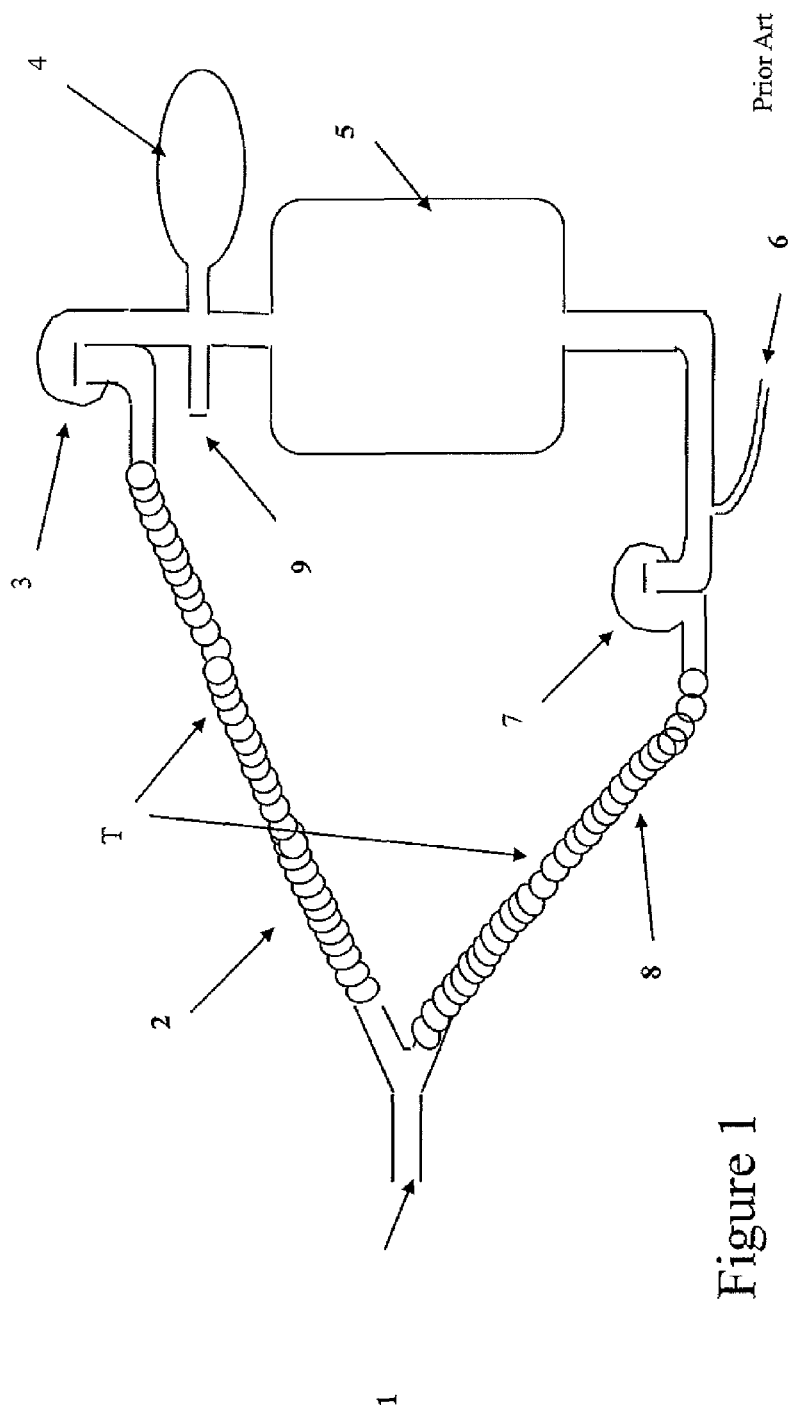
FIG. 1 is a circle circuit for performing anesthesia as known in the art. The circuit is designed to efficiently deliver anesthetic gases to a patient. It does so by allowing the patient to rebreathe the exhaled anesthetic gases but not $CO_2$.
Figure 1B:
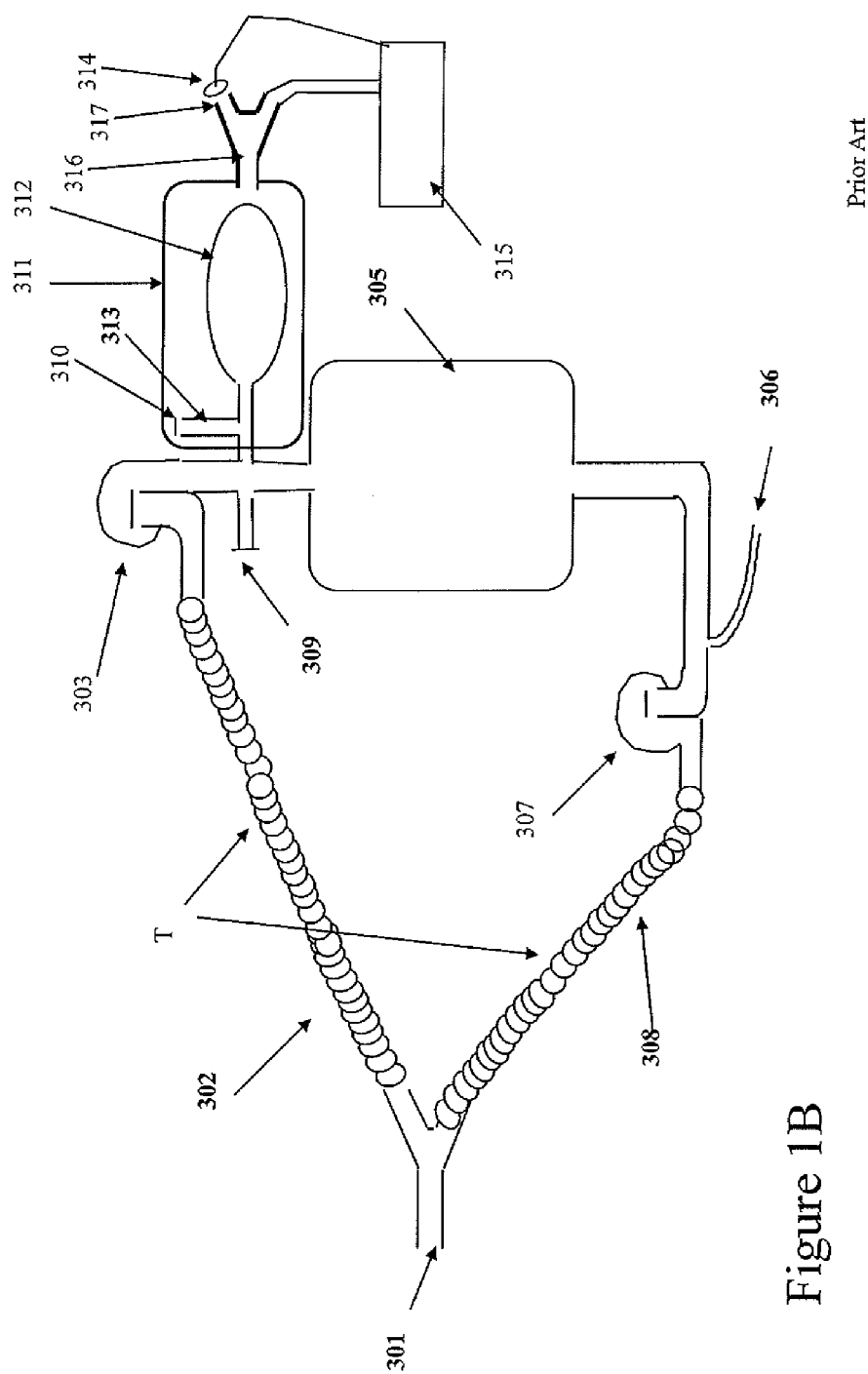
FIG. 1B a circle circuit for performing anesthesia for use with a mechanically ventilated patient, as known in the art. The circuit is designed to efficiently deliver anesthetic gases to a patient. It does so by allowing the patient to rebreathe exhaled anesthetic gases but not $CO_2$.
Figure 2:
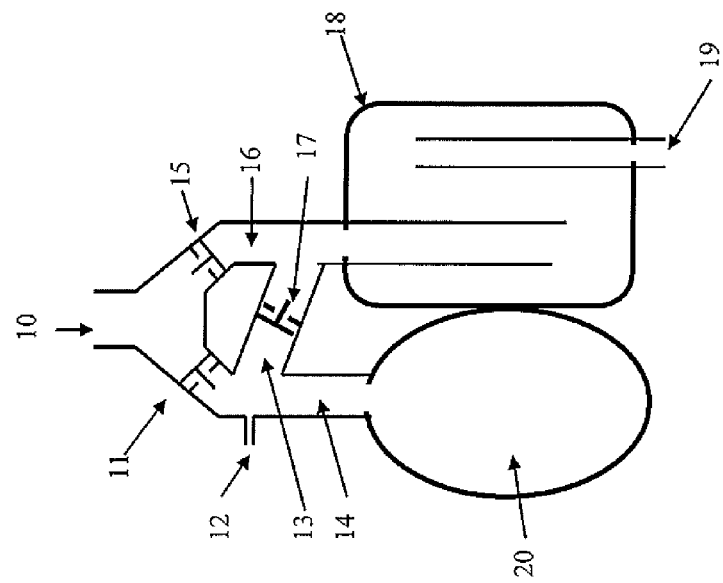
FIG. 2 is a SGDB Circuit as taught by Fisher in U.S. Pat. No. 6,622,725.
Figure 7:
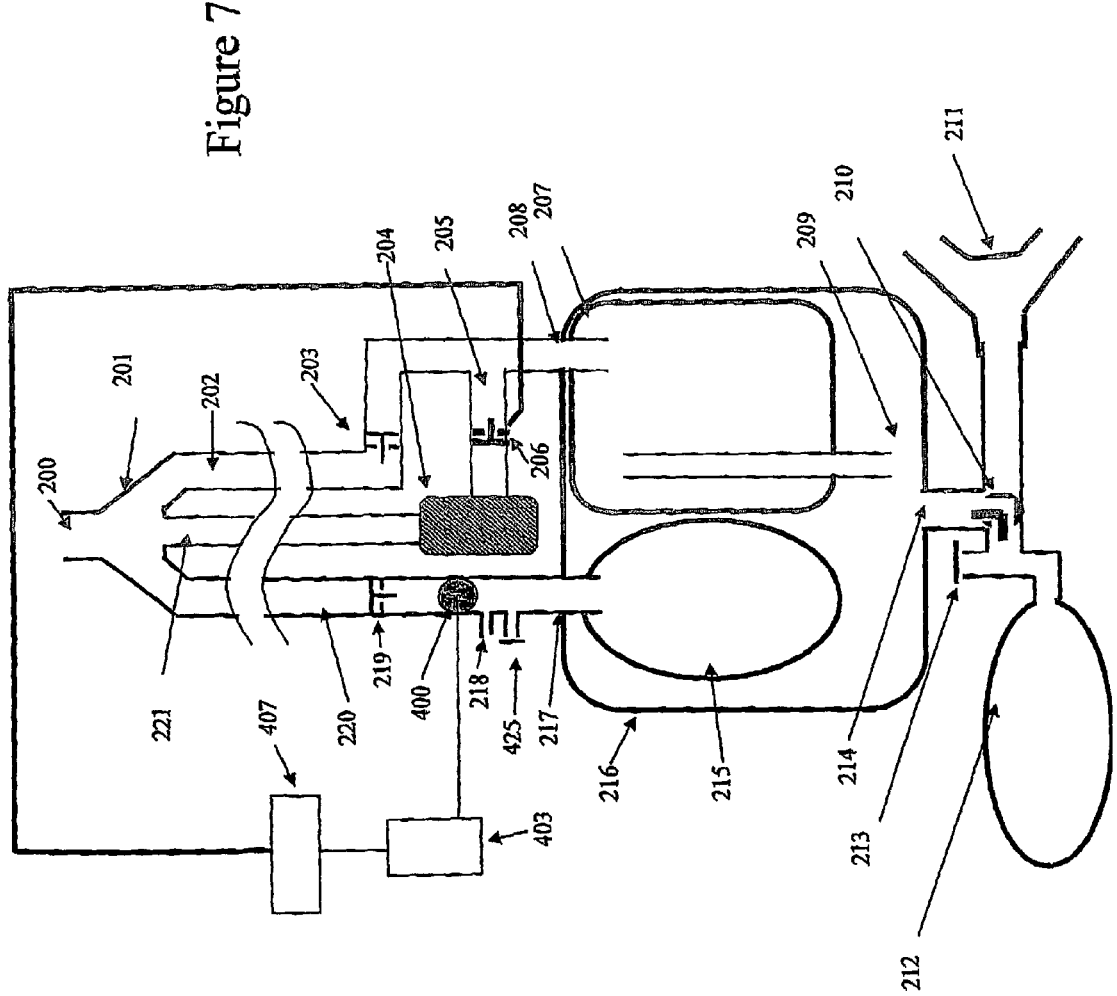
FIG. 7 is a new circuit designed to allow measurement of cardiac output while delivering anesthetics or removing volatile agents from a patient.

The primary difference between the standard anesthetic circle circuit of the prior art FIGS. 1, 1B) and the circuits disclosed herein is that with the circuits disclosed herein, both a SGS reservoir (18) and a FGS reservoir (20) are in the rigid box. With the valve configurations disclosed herein, there will be sequential delivery of the FGS, then the SGS, when $\dot{V}_E$ exceeds the FGSF. This does not occur with the standard anesthetic circle circuit, even if the $CO_2$ absorber is removed from the circuit Modification of Second Gas Set FIG. 7 shows the preferred circuit for measuring cardiac output while maintaining the ability to modify the SGS. The circuit consists of the following components:

200 Patient port
201 Three-port connector
202 expiratory limb
203 expiratory valve
204 cannister on bypass conduit that may be switched to be empty, contain $CO_2$ absorbing crystals, zeolyte, charcoal or similar substance that filters anesthetic agents, or hopcalite for filtering carbon monoxide
205 bypass conduit.
206 one-way bypass valve with opening pressure slightly greater than that of the inspiratory valve (219)
207 SGS reservoir bag
208 port in rigid container for entrance of expiratory limb of circuit in an air-tight manner
209 exit port for expired gas from expired gas reservoir
210 a 2-way manual valve that can be turned so that the gas in the rigid box (216) is continuous with either the ventilator Y piece (211) or the manual ventilation assembly consisting of ventilating bag (212) and APL valve (213)
211 the ventilator Y piece
212 the ventilation bag
213 APL valve
214 ventilation port in rigid box (216)
215 FGS reservoir
216 rigid box 217 port in rigid container for entrance of inspiratory limb of circuit (220) in an air-tight manner
218 FGS inlet port
219 inspiratory valve
220 inspiratory limb
221 bypass limb proximal to canister (204)
400 active FGS Control valve
403 valve control means
407 bypass valve opening sensing means Function of the Circuit as an Anesthetic Circuit:

For spontaneous ventilation, 3-way valve (210) is open between rigid container (216) and manual ventilation assembly consisting of ventilation bag (212) and APL valve (213). When the patient exhales, increased pressure in the circuit doses inspiratory valve (219) and bypass valve (206). Exhaled gas is directed into the exhalation limb (202), past one-way valve (203) into the expiratory reservoir bag (207). FGS enters via port (218) and fills the FGS reservoir (215). During inhalation, inhalation valve (219) opens and FGS from the FGS reservoir (215) and FGS port (218) enter the inspiratory limb (220) and are delivered to patient. If FGSP is less than $\dot{V}_E$, the FGS reservoir (215) empties before the end of the breath; continued respiratory effort results in a further reduction in pressure in the circuit. When the opening pressure of the bypass valve (206) is exceeded, it opens and gas from the expiratory gas reservoir (207) passes through the canister (204) into the rebreathing limb (221) and makes up the balance of the breath with SGS. The opening of bypass valve (206) is detected by valve opening sensing means (407) signals are sent to close FGS control valve (400) by activating valve control means (403). When the FGS control valve (400) is closed, any additional FGSF entering the circuit during the balance of inspiration is directed only to the FGS reservoir bag (215) and not to the patient. When valve (400) is closed patient receives only SGS for the balance of inspiration. FGS control valve (400) may be reopened any time from the beginning of expiration to just before the next inspiration. Phase of ventilation is sensed by sensor (407).

For the purposes of functioning as an anesthetic delivery circuit, part of the FGS entering the circuit would be the anesthetic vapor, for example Desflurane, and the canister (204) would contain $CO_2$ absorbent material. The SGS passes through the canister (204) but still contains expired $O_2$ and anesthetic, which can both be safely rebreathed by the patient. In this respect, the circuit in FIG. 7 functions like a circle anesthetic circuit in which the FGSF containing $O_2$ and anesthetic can be reduced to match the consumption or absorption by the patient. However, by bypassing the canister (204), the circuit can be used for measuring cardiac output.

If the canister (204) is filled with hopcalite it can be used to remove carbon monoxide from the patient, since the SGS still contains expired $O_2$ and $CO_2$. If the canister (204) is filled with zeolite it can be used to remove volatile agents such as anesthetics from the patient.

Advantages of Circuit Over Previous Art:
1) It is comparable to the circle anesthesia circuit with respect to efficiency of delivery of anesthesia, and ability to conduct anesthesia with spontaneous ventilation as well as controlled ventilation.
2) It is often important to measure tidal volume and $\dot{V}_E$ during anesthesia. With a circle circuit, a pneumotach with attached tubing and cables must be placed at the patient interface, increasing the dead-space, bulk and clutter at the head of the patient. With our circuit, the pneumotachograph (or a spirometer if the patient is breathing spontaneously) can be placed at port (214) and thus remote from the patient.
3) Sasano (Anesth Analg 2001; 93(5):1188-1191) taught a circuit that can be used to accelerate the elimination of anesthesia. However that circuit required additional devices such as an external source of gas (reserve gas), a demand regulator, self-inflating bag or other manual ventilating device, 3-way stopcock and additional tubing. Furthermore, Sasano did not disclose a method whereby mechanical ventilation can be used. In fact it appears that it cannot be used-patients must be ventilated by hand for that method. With the apparatus and method disclosed herein, there is no requirement for an additional external source of gas or demand regulator;
4) the patient can be ventilated with the ventilation bag (212) already on the circuit or the circuit ventilator, or any ventilator; no other tubing or devices are required.
5) Circle circuits cannot deliver FGS and then SGS sequentially. Such control is required to make physiological measurements such as cardiac output during anesthesia.

With the circuit of FIG. 7, if the canister (204) is bypassed, the circuit becomes the equivalent of the one described in FIG. 5 with the addition of the ventilator apparatus shown in FIG. 4. With the circuit of FIG. 7, box (216) could be opened to atmosphere instead of connected to a ventilator, and the circuit could be used with spontaneously breathing patients for measuring cardiac output while modifying SGS.

It should be recognized to those skilled in the art that various embodiments of the invention disclosed in this patent application are possible without departing from the scope including, but not limited to:
a) using multiple inspiratory and expiratory limbs in combination provided that:
   i) the inspiratory and expiratory limbs are kept separate except at a single point prior to reaching the patient where they are joined
   ii) each limb has the corresponding valves as in the arrangement above, and
   iii) the valves have the same relative pressures so as to keep the inspired gas delivery sequential as discussed above.
b) using active valves, for example electronic, solenoid, or balloon valves, instead of passive valves, provided said valves are capable of occluding the limbs, and means is provided for triggering and controlling said active valves. The advantage of active valves is more precise control. The disadvantage is that they are more costly.
c) replacing reservoir bags with extended tubes or other means for holding gases
d) surrounding valves in exhalation limb and/or in the inspiratory limb of circuit with the exhaled gas reservoir causing them to be surrounded by warm exhaled air and prevent freezing and sticking of valves in cold environments.
e) Changing the composition of FGS and SGS to change alveolar concentrations of gases other than $CO_2$, for example $O_2$. By analogy to $CO_2$, with respect to $O_2$: alveolar $PO_2$ is determined by FGS flow and the $PO_2$ of FGS. When $PO_2$ of SGS is the same as the $PO_2$ in the alveoli, inhaling SGS does not change flux of $O_2$ in the alveoli. Therefore, those skilled in the art can arrange the partial pressure of component gases in FGS and SGS and the flows of FGS such that they can achieve any alveolar concentration of component gases independent of $\dot{V}_E$, as long as $\dot{V}_E$ exceeds sufficiently flow of FGS.

As many changes can be made to the various embodiments of the invention without departing from the scope thereof; it is intended that all matter contained herein be interpreted as illustrative of the invention but not in a limiting sense.

We claim:

1. A breathing circuit for use with a first gas set (FGS) and a second gas set (SGS), said circuit comprising an inspiratory limb, an expiratory limb, an FGS reservoir and a flow control system for sequentially delivering to a patient on inspiration, first the FGS, free of SGS, and, when the FGS reservoir is emptied, SGS free of FGS, for a balance of inspiration, wherein the inspiratory limb operatively connected to the FGS reservoir, and wherein the flow control system includes at least one first valve operatively associated with the expiratory limb for preventing inhalation of SGS during delivery of the FGS and at least one second valve operatively associated with the inspiratory limb to prevent inhalation of FGS during delivery of the SGS.

2. A breathing circuit according to claim 1, wherein the expiratory limb is operatively associated with an SGS reservoir and wherein the at least one first valve includes a one way expiratory valve operatively associated with the expiratory limb for preventing flow of SGS from the SGS reservoir to the patient during inspiration of the FGS and a bypass valve operatively associated with the SGS reservoir and a bypass limb, the bypass valve bypassing the one way expiratory valve to allow flow of SGS from the SGS reservoir to the patient for the balance of inspiration.

3. The breathing circuit of claim 2, wherein said bypass valve is configured to open during inspiration only once the FGS reservoir has been emptied.

4. The breathing circuit of claim 1, wherein the FGS reservoir is fluidly connected to and replenished via
   a port for entry of FGS, the at least one second valve preventing flow of FGS to the patient during delivery of the SGS and replenishment of the FGS reservoir.

5. The breathing circuit of claim 4, wherein the inspiratory limb is operatively associated with at least one uni-directional valve that opens toward the patient for preventing gas exhaled by the patient from entering the inspiratory limb.

6. The breathing circuit of claim 1, wherein the at least one second valve is activated by a control means, which allows FGS to flow to the subject during inspiration until the FGS reservoir has been emptied and then prevents FGS from flowing to the subject until the next inspiration begins.

7. The breathing circuit of claim 6, where the flow control system additionally comprises at least one unidirectional valve that opens toward the patient, located between the at least one second valve and the patient.

8. The breathing circuit of claim 6, additionally comprising means for detecting when SGS is being delivered to the patient, the control means using said detecting means to determine when to direct FGS to the FGS reservoir and prevent FGS from being delivered to the patient.

9. The breathing circuit of claim 1, wherein the at least one first valve is operatively associated with a control means, said control means configured to immediately open said at least one first valve to allow SGS to be inspired by the subject during inspiration once the inspiratory reservoir has been emptied and to closes said at least one first valve after expiration.

10. The breathing circuit of claim 1, comprising a SGS reservoir, wherein the FGS reservoir and SGS reservoir are contained in a sealed container having respective openings for the inspiratory limb and the expiratory limb, the container also having an opening for connection to a ventilator.

11. A breathing circuit comprising:
   a) an inspiratory limb with a port for entry of a first gas set (FGS), a FGS reservoir for making FGS available to a patient for a first portion of inspiration and FGS flow control means, whereby the FGS control means directs FGS into the FGS reservoir during a second portion of inspiration after the FGS reservoir is emptied preventing FGS flow to the patient prior to a beginning of a next first portion of inspiration,
   b) an expiratory limb containing an exit port for exhaled gas, an SGS reservoir, and an exhalation valve for directing the flow towards the SGS reservoir during exhalation,
   c) a bypass limb containing a bypass flow control means which directs flow of the SGS from the SGS reservoir to the patient during the second portion of inspiration from when the FGS reservoir is emptied until the end of inspiration.

12. The breathing circuit of claim 11, where the FGS flow control means comprises at least one uni-directional valve that opens toward the patient.

13. The breathing circuit of claim 11, where the FGS flow control means comprises a FGS controlled-valve activated by a FGS valve control means, which allows FGS to flow to the patient during inspiration until the FGS reservoir has been emptied and then prevents FGS from flowing to the patient until the next inspiration begins.

14. The breathing circuit of claim 13, where the FGS flow control means additionally comprises at least one uni-directional valve that opens toward the patient, located between the FGS controlled-valve and the patient.

15. The breathing circuit of claim 13, additionally comprising means for detecting when SGS is being delivered to the patient, the FGS flow control means using said detecting means to determine when to direct FGS to the FGS reservoir and prevent FGS from being delivered to the patient.

16. The breathing circuit of claim 11, wherein the inspiratory limb and the expiratory limb are co-axial.

17. The breathing circuits of claim 16, wherein one of the limbs is comprised of a material that allows passage of moisture to the other but keeps the gases in the limbs separate.

18. The breathing circuits of claim 11, wherein the FGS reservoirs and the SGS reservoir are contained in a sealed container having respective openings for the inspiratory limb and the expiratory limb, the container also having an opening for connection to a ventilator.

19. A breathing circuit for use with a first gas set (FGS) and a second gas set (SGS), said circuit comprising an inspiratory limb, an FGS reservoir operatively connected to the inspiratory limb, an expiratory limb fluidly connected to a SGS reservoir and a bypass limb, and a flow control system for sequentially delivering to a patient on inspiration, first the FGS, free of SGS, and, when the FGS reservoir is emptied, SGS free of FGS, for a balance of inspiration, wherein the flow control system includes a plurality of flow control means configured to prevent inhalation of SGS during a first portion of inspiration and FGS during the balance of inspiration, the plurality of flow control means including a bypass valve operatively associated with the bypass limb, the bypass valve configured to allow the patient to inspire gas exhaled in a preceding breath upon depletion of the FGS reservoir, for the balance of inspiration.

* * * * *